(12) United States Patent
Ng et al.

(10) Patent No.: US 10,299,879 B2
(45) Date of Patent: May 28, 2019

(54) SYSTEM AND METHOD FOR ALIGNING AN ELONGATED TOOL TO AN OCCLUDED TARGET

(71) Applicant: NDR MEDICAL TECHNOLOGY PTE. LTD., Singapore (SG)

(72) Inventors: Ka Wei Ng, Singapore (SG); Jin Quan Goh, Singapore (SG); Ting Liu, Singapore (SG)

(73) Assignee: NDR MEDICAL TECHNOLOGY PTE. LTD., Primz Bizhub (SG)

( * ) Notice: Subject to any disclaimer, the term of this patent is extended or adjusted under 35 U.S.C. 154(b) by 168 days.

(21) Appl. No.: 15/581,706

(22) Filed: Apr. 28, 2017

(65) Prior Publication Data

US 2018/0200015 A1 Jul. 19, 2018

(30) Foreign Application Priority Data

Jan. 17, 2017 (SG) .............................. 10201700386P

(51) Int. Cl.
| | |
|---|---|
| *G06K 9/00* | (2006.01) |
| *A61B 90/11* | (2016.01) |
| *A61B 34/20* | (2016.01) |
| *A61B 34/30* | (2016.01) |
| *A61B 90/00* | (2016.01) |

(52) U.S. Cl.
CPC .............. *A61B 90/11* (2016.02); *A61B 34/20* (2016.02); *A61B 2034/2051* (2016.02); *A61B 2034/2055* (2016.02); *A61B 2034/304* (2016.02); *A61B 2090/374* (2016.02); *A61B 2090/3762* (2016.02); *A61B 2090/3966* (2016.02)

(58) Field of Classification Search
CPC ...... A61B 2034/2055; A61B 2034/304; A61B 2090/3966; A61B 34/20; A61B 90/11
USPC .......................................... 382/128; 128/898
See application file for complete search history.

(56) References Cited

U.S. PATENT DOCUMENTS 9,905,000 B2 * 2/2018 Chou .................... A61B 90/37

OTHER PUBLICATIONS

Noah J. Cowan et al., "Robotic Needle Steering: Design, Modeling, Planning, and Image Guidance", dated 2011, 26 pages.
(Continued)

*Primary Examiner* — Charlotte M Baker
(74) *Attorney, Agent, or Firm* — Hickman Palermo Becker Bingham LLP

(57) ABSTRACT

Systems and methods for aligning an elongated tool to an occluded target and for striking the occluded target using the elongated tool are disclosed. The system for aligning an elongated tool to an occluded target includes an adjustment mechanism configured to adjust an angular orientation of the elongated tool relative to a pivot point spaced from the target; a 3-dimensional (3D) imaging device configured to capture a 3D image of the elongated tool and the occluded target; and a processor communicatively coupled with the adjustment mechanism and the 3D imaging device. The processor is configured to process the 3D image received from the 3D imaging device to obtain location data of the target and the pivot point; and based on the location data of the target and the pivot point, control the adjustment mechanism to adjust the angular orientation of the elongated tool relative to the pivot point to align a longitudinal axis of the elongated tool with the target and the pivot point.

20 Claims, 7 Drawing Sheets

(56) References Cited

OTHER PUBLICATIONS

Momen Abayazid et al., "Experimental Evaluation of Ultrasound-Guided 3D Needle Steering in Biological Tissue", dated 2014, 14 pages.

* cited by examiner

SYSTEM AND METHOD FOR ALIGNING AN ELONGATED TOOL TO AN OCCLUDED TARGET

BENEFIT CLAIM

This application claims the benefit under 35 U.S.C. § 119 of Singapore patent application 10201700386P, filed 17 Jan. 2017, the entire contents of which are hereby incorporated by reference for all purposes as if fully set forth herein.

FIELD OF INVENTION

The present invention relates broadly to a system and method for aligning an elongated tool to an occluded target.

BACKGROUND

Many clinical practices involve percutaneous insertion of needles for biopsy and drug delivery by placing the tip of the needle safely and accurately in a lesion, organ, or vessel. Examples of treatments requiring needle insertions include vaccinations, blood/fluid sampling, regional anesthesia, tissue biopsy, catheter insertion, cryogenic ablation, electrolytic ablation, brachytherapy, neurosurgery, deep brain stimulation, and various minimally invasive surgeries (MIS). Conventionally, these surgical operations are carried out by a surgeon holding the trocar needle in his hand with one end of the trocar resting on a patient's skin. The other end of the trocar is tilted numerous times to establish an accurate alignment between the trocar and the target area. The alignment of the trocar is usually determined with the help of a medical imaging system such as X-ray radiography, magnetic resonance imaging (MRI), medical ultrasonography or ultrasound, computed tomography (CT) and others. Once the accurate alignment is confirmed, the surgeon has to maintain the alignment of the trocar by steadying his hand. The trocar is subsequently pushed into the patient's body to reach the target area. Targeting accuracy is crucial because poor placement of the trocar during biopsies leads to false negatives. Inaccurate seed placement during brachytherapy destroys healthy tissues instead of cancerous tissues, sometimes with catastrophic outcomes.

An example of these surgical operations is percutaneous renal surgery. Percutaneous renal surgery is a minimally invasive procedure for establishing a keyhole access in percutaneous nephrolithotomy (PCNL) to remove a kidney stone. In this procedure, a trocar is passed through a patient's skin through the body layers into the kidney to reach a stone target. Surgical instruments such as guidewire, ultrasonic probes and vacuum are then passed through the hole in the trocar to carry out the stone removal process.

The duration of the trocar insertion procedure typically ranges from 10 minutes to 1.5 hours and throughout the procedure, the C-arm fluoroscope has to be in operation. Consequently, both the patient and surgical crew are subjected to long exposure of X-ray and this could be a potential health hazard in the long run. In addition, due to the elaborate procedure, there may be instances when the trocar has to be withdrawn and the entire procedure needs to be repeated. This may aggravate the condition of the patient as multiple punctures of the patient's body may increase the risks to the patient such as significant bleeding, hematoma formation and infection. The procedure may have to be called off and rescheduled, thus causing much distress to the patient and loss of precious time of the healthcare professionals.

To address the problems above, robotic arms are used to perform the trocar insertion procedure. For example, current approaches utilize robotic arm surgical systems which mimic the standard manual procedure. In other words, the systems are manually controlled by the surgeon, e.g. using a manipulator such as a joystick, to align the trocar with the target area. Also, these conventional systems are bulky and slow in processing. It is also expensive to manufacture the systems and implement the trocar insertion procedure using the systems.

Alternatively, the surgical procedures may be carried out using a robotic system that controls a flexible needle with steering capabilities in subsurface tissues under image feedback to reach a target in the patient's body. A variety of mechanisms may be used to steer the flexible needle, e.g. tip-based steering, lateral manipulation of the needle base and tissue manipulation as the needle is being inserted. Flexible needles can be used to steer around hard or sensitive tissues such as blood vessels and bones, allowing targets that are inaccessible by a straight-line path to be reached by the needles. Subsurface needle steering may also allow the trajectory of the needle to be manipulated, thus avoiding the need for repeating the whole surgical procedures. However, this technique is still time-consuming and requires iterative images to be obtained and processed.

A need therefore exists to provide a system for aligning a surgical tool that seeks to address at least some of the above problems.

SUMMARY

According to a first aspect of the present invention, there is provided a system for aligning an elongated tool to an occluded target, the system comprising:

an adjustment mechanism configured to adjust an angular orientation of the elongated tool relative to a pivot point spaced from the target;

a 3-dimensional (3D) imaging device configured to capture a 3D image of the elongated tool and the occluded target; and a processor communicatively coupled with the adjustment mechanism and the 3D imaging device, wherein the processor is configured to:
  process the 3D image received from the 3D imaging device to obtain location data of the target and the pivot point; and
  based on the location data of the target and the pivot point, control the adjustment mechanism to adjust the angular orientation of the elongated tool relative to the pivot point to align a longitudinal axis of the elongated tool with the target and the pivot point.

The processor may be further configured to:
process the 3D image to generate a sectional view, wherein the sectional view comprises at least one sectioning plane passing through the target; and
extract the location data of the target based on image data of the sectional view.

The at least one sectioning plane may comprise an x-axis sectioning plane and a y-axis sectioning plane perpendicular to the x-axis sectioning plane, and wherein both the x-axis and the y-axis sectioning planes pass through the target.

The location data may comprise target coordinates in 3D Euclidean space and wherein the processor may be configured to extract the target coordinates based on the target location on the sectional view.

The processor may be further configured to:
extract pivot point coordinates based on the 3D image;

calculate a straight line passing through the target coordinates and the pivot point coordinates; and control the adjustment mechanism to adjust the angular orientation of the elongated tool to align the longitudinal axis of the surgical tool with the straight line.

The processor may be further configured to calculate a distance between the pivot point and the target based on the target coordinates and the pivot point coordinates.

The processor may be further configured to simulate a trajectory of the elongated tool toward the target using the distance and adjusted angular orientation of the elongated tool.

The 3D image may be a real-time 3D image and wherein the 3D imaging device may comprise at least one selected from a group consisting of a magnetic resonance imaging (MRI) machine, a computerized tomography (CT) scanner and a fluoroscope.

The adjustment mechanism may comprise a base and a platform, wherein the platform may be configured to be parallel to the base.

The adjustment mechanism may further comprise a plurality of arms linking the base with the platform, the plurality of arms may be configured to move the platform along a plane parallel to the base to adjust the angular orientation of the elongated tool relative to the pivot point.

The platform may comprise a ball joint compliance for supporting the elongated tool, the ball joint compliance may comprise a hole configured to allow sliding movement of the elongated tool therethrough.

The adjustment mechanism may further comprise a tool holder detachable from the platform.

According to a second aspect of the present invention, there is provided a system for striking an occluded target using an elongated tool, the system comprising:

an alignment system as defined in the first aspect; and an actuator coupled to the elongated tool, wherein the processor is further configured to determine a striking distance between the pivot point and the target; and wherein the actuator is configured to drive the elongated tool toward the target based on the angular orientation of the elongated tool at alignment and the striking distance.

The system may further comprise a display device coupled to the processor, wherein the processor may be further configured to simulate a trajectory of the elongated tool based on the angular orientation of the elongated tool at alignment and the striking distance for display on the display device.

The system may further comprise a stopper configured to be mounted to the elongated tool and to prevent further movement of the elongated tool beyond the striking distance.

According to a third aspect of the present invention, there is provided a method of aligning an elongated tool to an occluded target, the method comprising the steps of:

capturing a 3-dimensional (3D) image of the elongated tool and the occluded target;

processing the 3D image to obtain location data of the target and a pivot point spaced from the target; and based on the location data of the target and the pivot point, adjusting an angular orientation of the elongated tool relative to the pivot point to align a longitudinal axis of the elongated tool with the target and the pivot point.

Processing the 3D image to obtain location data of the target may comprise the steps of:

generating a sectional view, wherein the sectional view comprises at least one sectioning plane passing through the target; and extracting the location data of the target based on image data of the sectional view.

The at least one sectioning plane may comprise an x-axis sectioning plane and a y-axis sectioning plane perpendicular to the x-axis sectioning plane, and wherein both the x-axis and the y-axis sectioning planes pass through the target.

Extracting the location data of the target may comprise extracting target coordinates in 3D Euclidean space based on the target location on the sectional view.

The method may further comprise the steps of:

extracting pivot point coordinates based on the 3D image;

calculating a straight line passing through the target coordinates and the pivot point coordinates; and controlling the adjustment mechanism to adjust the angular orientation of the elongated tool to align the longitudinal axis of the surgical tool with the straight line.

According to a fourth aspect of the present invention, there is provided a method of striking an occluded target using an elongated tool, the method comprising the steps of:

aligning a longitudinal axis of the elongated tool with the target using the method as defined in the third aspect;

calculating a striking distance between the pivot point and the target based on the location data of the pivot point and the tip; and advancing the elongated tool toward the target according to the calculated distance.

Prior to the step of advancing the elongated tool toward the target, the method may comprise the step of simulating a trajectory of the elongated tool toward the target according to the angular orientation of the elongated tool at alignment and the striking distance.

The method may further comprise stopping further movement of the elongated tool beyond the striking distance.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
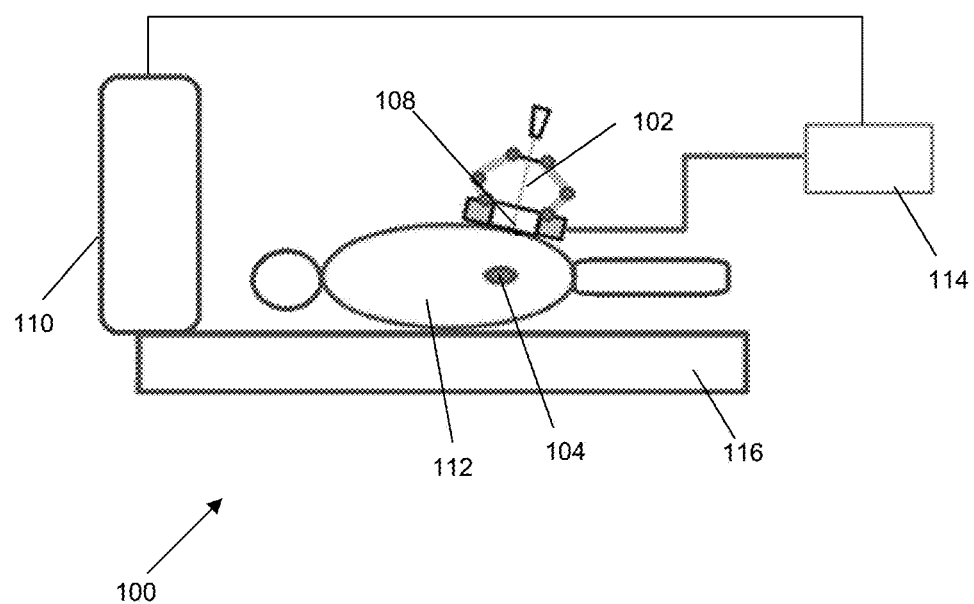
FIG. 1 shows a schematic diagram illustrating a system for aligning an elongated tool to an occluded target according to an example embodiment.

FIG. 1 shows a schematic diagram illustrating a system 100 for aligning an elongated tool, for example a surgical tool 102 such as a hollow needle, to an occluded target 104 according to an example embodiment. In the description that follows, the occluded target is a kidney stone 104 and the system 100 is described with reference to a surgical application for removing the kidney stone 104. However, it will be appreciated that the system 100 can be used in numerous other applications, such as biopsy, ablation and vertebroplasty. Further, other non-surgical applications such as those performed in the laboratories or industry are also envisaged.

The system 100 comprises an adjustment mechanism 106. The adjustment mechanism 106 is configured to adjust an angular orientation of the surgical tool 102 relative to a pivot point 108. The system 100 further comprises an imaging device, in the form of a 3-dimensional (3D) imaging device 110, configured to capture a 3D image of the surgical tool 102 and a patient's body 112 containing the kidney stone 104. The 3D image captured by the 3D imaging device 110 comprises an image of the inside of the patient's body 112.

The system 100 further comprises a processor 114 communicatively coupled with the adjustment mechanism 106 and the 3D imaging device 110. The processor 114 is configured to process the 3D image received from the 3D imaging device 110 to obtain location data of the kidney stone 104. Based on the location data of the kidney stone 104, the processor 114 can control the adjustment mechanism 106 to adjust the angular orientation of the surgical tool 102 relative to the pivot point 108 to align a longitudinal axis of the surgical tool 102 with the kidney stone 104 and the pivot point 108.

In this embodiment, the adjustment mechanism 106 is mounted on the patient's body 112 lying on a surgical table 116, e.g. using adhesive tape or gel. In other words, the adjustment mechanism 106 is not connected to a fixed structure, but rather, can be positioned at a desired place relative to the patient's body 112 for the required type of surgery. The adjustment mechanism 106 mounted on the patient's body 112 may move in tandem with the breathing movement of the patient's abdomen. This may minimize skin and organ rupture during the operation when the surgical tool 102 is in the patient's body 112. In other embodiments, the adjustment mechanism 106 may be mounted to a rigid structure above the patient's body 112 and surgical table 116 to fix the position of the adjustment mechanism 106. The adjustment mechanism 106 includes at least one actuator (not shown) that is configured to operate the adjustment mechanism 106 when the actuator receives signals from the processor 114 via a wireless connection. In yet another embodiment, the signals from the processor 114 may also be transmitted to the actuator via a wired connection.

The 3D imaging device 110 may capture real-time 3D image of the surgical tool 102 and the patient's body 112 containing the kidney stone 104. The position on the skin of the patient's body 112 adjacent to the kidney stone 104 is typically marked with an "X" mark as the insertion point of the surgical tool 102. In an embodiment, the "X" mark is the pivot point 108 where a tip of the surgical tool 102 is placed when the angular orientation of the surgical tool 102 is being adjusted by the adjustment mechanism 106. Some examples of the 3D imaging device 110 include magnetic resonance imaging (MRI) machine, computerized tomography (CT) scan and fluoroscope.

The processor 114 is communicatively coupled to the 3D imaging device 110 to receive the 3D image data transferred via e.g. a wired/wireless connection or a data storage device (USB flash drive). From the 3D image data, the processor 114 can extract information such as location data of the kidney stone 104 and the pivot point 108. The location data in the example embodiments is the Cartesian coordinates of the kidney stone 104 and the pivot point 108 in 3D Euclidean space. Specifically, the 3D image received from the 3D imaging device 110 is opened in a 3D plane-sectioning software. On the 3D image, a clinician selects at least one sectioning plane, e.g. X-axis or y-axis sectioning plane, which passes through the kidney stone 104. A sectional view of the patient's body 112 is generated based on the sectioning plane selected by the clinician by removing the image of the body parts that are obstructing the kidney stone 104, making the kidney stone 104 visible on a sectioned surface on the 3D image.

The clinician then selects the kidney stone 104 on the sectional view. The processor 114 is configured to determine the coordinates of the kidney stone 104 based on the location of the kidney stone 104 selected by the clinician on the sectional view. From the 3D image data, the clinician may also select the location of the pivot point 108 where the tip of the surgical tool 102 is placed and the processor 114 is configured to determine the coordinates of the pivot point 108. Based on the coordinates of the kidney stone 104 and the pivot point 108, the processor can determine a straight line running through the target coordinates and the pivot point coordinates. After determining the straight line, the processor can control the adjustment mechanism 106 to adjust the angular orientation of the surgical tool 102 relative to the pivot point 108 to align the longitudinal axis of the surgical tool 102 with the straight line.

Based on the coordinates of the kidney stone 104 and the pivot point 108, the processor 114 can calculate a distance between the tip of the surgical tool 102 at the pivot point 108 and the kidney stone 104. After calculating the distance, the processor 114 can simulate a trajectory of the surgical tool 102 toward the kidney stone 104 using the 3D image according to the distance calculated. If the simulation result is satisfactory, the surgical tool 102 is inserted into the patient's body 112 according to the distance calculated.

It will also be appreciated that the processor 114 may be configured to scan the 3D image received from the 3D imaging device 110 and, without any input from the clinician, automatically process the 3D image to create the sectional view. Further, the processor 114 may, without any input from the clinician, automatically obtain the location of the kidney stone 104 on the sectional view, to determine the coordinates of the kidney stone 104 and pivot point 108 and to calculate the distance between the kidney stone 104 and the pivot point 108. In addition, in the case that the tip of the surgical tool 102 is not placed on the pivot point 108 when the angular orientation of the surgical tool 102 is being adjusted but move relative to the pivot point 108, the processor may be configured to extract the location data of the tip, in the form of point coordinates. Accordingly, instead of using the coordinates of the pivot point 108, the processor can determine or update the straight line and the distance between the tip of the surgical tool 102 and the kidney stone 104 using the coordinates of the tip and the kidney stone 104.

Figure 2A:
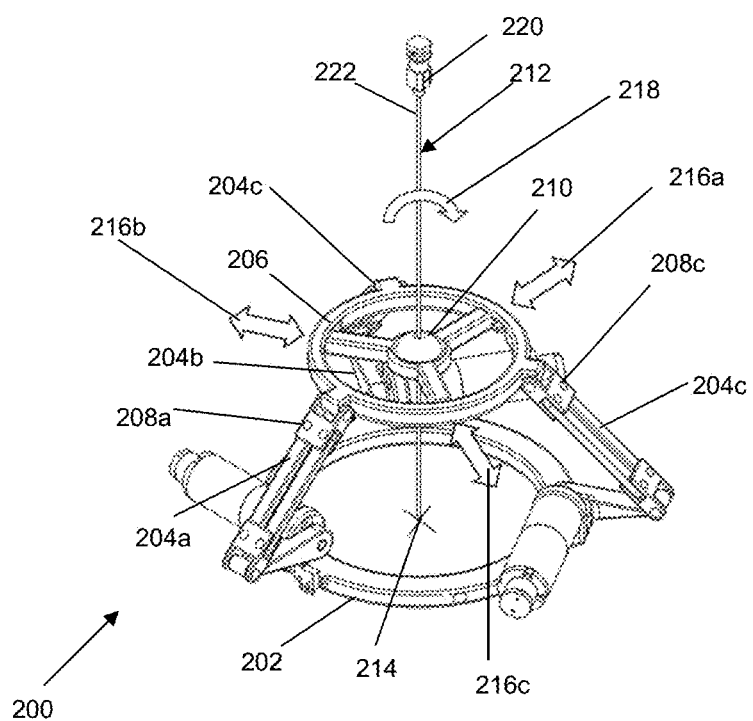
FIG. 2A shows a perspective view of an adjustment mechanism for use in the system of FIG. 1 according to an example embodiment.
Figure 2B:
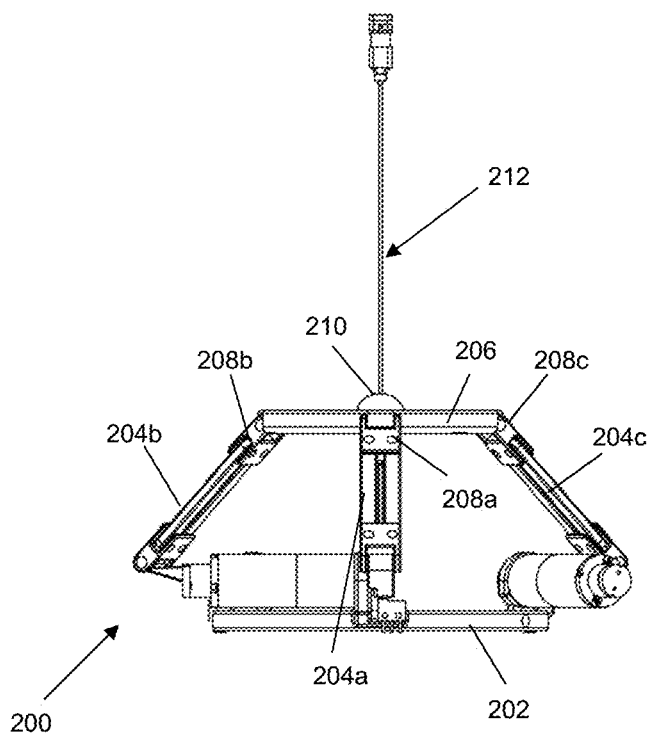
FIG. 2B shows a front view of the adjustment mechanism of FIG. 2A.

FIG. 2A and FIG. 2B show a perspective view and front view respectively of an adjustment mechanism 200 suitable for use in the system 100 of FIG. 1 according to an example embodiment. The adjustment mechanism 200 comprises a base 202, in the form of an annular ring, and a plurality of arms, represented as first arm 204a, second arm 204b and third arm 204c. The arms 204a, 204b, 204c are connected to the base 202 at a substantially uniform angular distance from each other. The adjustment mechanism 200 further comprises a raised platform 206. The raised platform 206 is connected to end effectors 208a, 208b, 208c of the arms 204a, 204b, 204c respectively. The platform 206 is in the form of an annular ring and comprises a ball joint compliance 210 at the center of the platform 206. The ball joint compliance 210 comprises a hole which holds a surgical tool 212 and allows sliding movement of the surgical tool 212. The ball joint compliance 210 further comprises a drive mechanism, in the form of a plunger (not shown), for holding and inserting the surgical tool 212 into a patient's body 112 (FIG. 1).

During operation, the base 202 is adhered to the patient's body 112. The arms 204a, 204b, 204c are actuated by at least one actuator (not shown) to coordinate with each other to adjust the position of the platform 206 and thus the orientation of the surgical tool 212 relative to the pivot point 214. The platform 206 typically moves at the same plane at a predetermined constant height relative to the base 202 during each operation, and the movement of the platform 206 relative to the base 202 is shown in FIG. 2A by arrows 216a, 216b, 216c. The height is normally determined at a calibration stage prior to the operation based on factors such as needle gauge, patient's physiology etc. When the position of the platform 206 is adjusted by the arms 204a, 204b, 204c, the surgical tool 212 is held loosely by the plunger and the ball joint compliance 210, allowing the surgical tool 212 to pivot or swivel freely about the pivot point 214. This configuration allows tilting of the surgical tool 212 when the platform 206 is moved at the same plane, and the tilting of the surgical tool 212 is shown by arrow 218 in FIG. 2A.

The surgical tool 212 in the example embodiments comprises an adjustable stopper 220 mounted adjacent to an end 222 of the surgical tool 212 opposite the pivot point 214. After the orientation of the surgical tool 212 and the depth of insertion are confirmed, the position of the ball joint compliance 210 is locked and the stopper 220 is affixed to the surgical tool such that the distance between the stopper 220 and the ball joint compliance 210 is approximately equal to the insertion depth. Next, the plunger is actuated by the actuator to hold and insert the surgical tool 212 into the patient's body 112. Typically, the depth of the insertion of the surgical tool 212 is restricted by the distance between the ball joint compliance 210 and the stopper 220. This configuration may restrict excessive insertion of the surgical tool 212 into the patient's body 112.

The structure of the adjustment mechanism 200 is typically made of light and rigid material. In some embodiments, the adjustment mechanism 200 is made of radiolucent material, such that the 3D image provided by the 3D imaging device 110 (FIG. 1) does not capture an image of the adjustment mechanism 200. In preferred embodiments, different parts of the adjustment mechanism 200 can be made of materials with different radiolucency. As an example, part of the platform 206 of the adjustment mechanism 200 is made of radiopaque material, e.g. stainless steel, while other parts of the adjustment mechanism 200 are made of radiolucent material. In this instance, the image of the platform 206 is captured on the 3D image by the 3D imaging device 110 and the location data of the platform 206 can be extracted from the 3D image. This may assist in adjusting the angular orientation of the surgical tool 212 and in determining the geometrical relationship between the planes formed by the platform 206 and other planes, such as the target plane of the kidney stone 104 (FIG. 1). In particular, the platform 206 includes a ball joint compliance 210 that holds the surgical tool 212 at the center of the platform 206. The location data of the platform 206 may allow easy determination of the coordinates of the ball joint compliance and thus, the angular orientation of the surgical tool 212. The process of the aligning the surgical tool 212 is thus easier.

As the adjustment mechanism 200 has a simple structure and is relatively small in size, it may move and respond fast to signals from the processor 114 (FIG. 1). The configuration of the adjustment mechanism 200 also restricts excessive movement. This may reduce the tearing of skin in the operation. In addition, most parts of the adjustment mechanism 200 are also made of biocompatible material, such that the use of the adjustment mechanism 200 in the surgery does not cause any undesirable effects to the patient. For example, the materials that may be suitable are titanium and polyether ether ketone (PEEK). However, it will be appreciated that the structure of the adjustment mechanism 200 may be made by other materials.

In an embodiment, the surgical tool 212 may comprise a tactile sensor (not shown) communicatively coupled to the processor 114 to detect pressure change on the surgical tool 212. This may enhance the accuracy of the processor 114 in detecting the depth of the surgical tool 212 in the patient's body 112 and detecting the kidney stone 104.

Figure 2C:
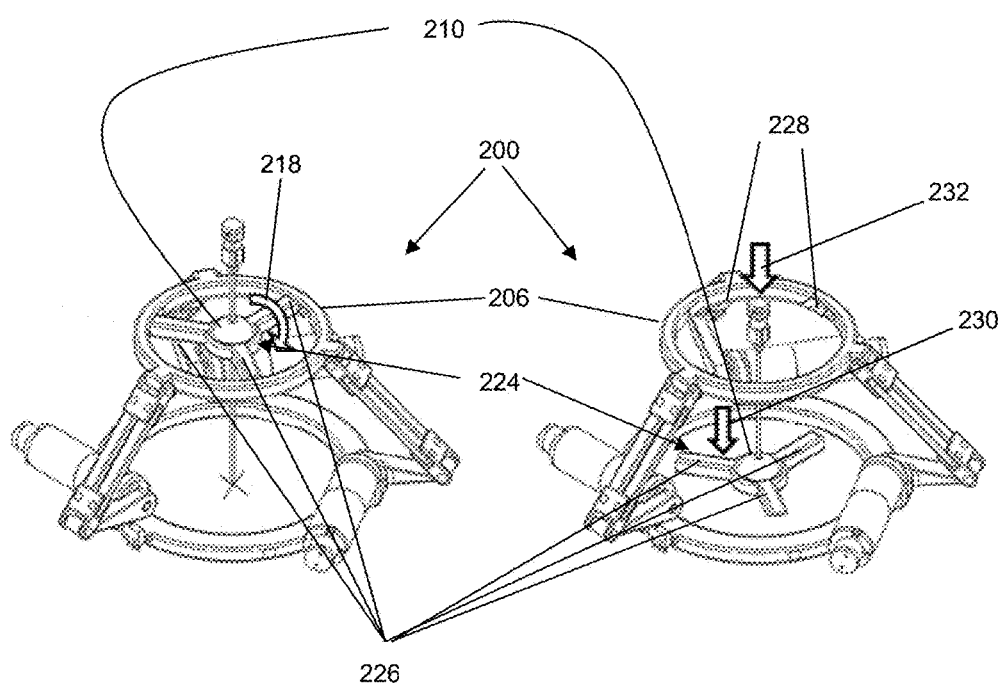
FIG. 2C shows two perspective views illustrating use of a tool holder of the adjustment mechanism of FIG. 2A according to an example embodiment.

FIG. 2C shows two perspective views illustrating use of a tool holder 224 of the adjustment mechanism of FIG. 2A according to an example embodiment. Here, the tool holder 224 is detachable from the platform 206. The structure of the tool holder 224 includes the ball joint compliance 210 and a plurality of supporting structures 226 extending radially outward from the ball joint compliance 210, linking the ball joint compliance 210 with the annular ring of the platform 206. An engagement mechanism, represented as catch 228, is used for detachably fastening the tool holder 224 to the platform 206.

As shown in the first arrangement (the left diagram on FIG. 2C), the tool holder 224 is attached to the platform 206 when the platform 206 is moved to tilt the surgical tool 212. The tilting of the surgical tool 212 is shown by arrow 218. As shown in the second arrangement (the right diagram on FIG. 2C), if further insertion is required beyond the insertion depth allowed by the stopper 220, the tool holder 224 is detached from the platform 206, e.g. by turning the tool holder 224 in the clockwise or anticlockwise direction, and lowered onto the patient's body 112, as shown by arrow 230. The tool holder 224 can be mounted on the patient's body 112 (FIG. 1), e.g. using adhesive tape or gel. After the tool holder 224 is mounted on the patient's body 112, the plunger is actuated by the actuator to hold and further insert the surgical tool 212 into the patient's body 112, as shown by arrow 232. At this point, the angular orientation of the surgical tool has been ascertained to be in alignment with the kidney stone. The tool holder 224 thus allows the surgical tool 212 to be inserted into the patient's body 112 to a greater depth, providing flexibility in the type of work to be carried out as required.

Figure 3:
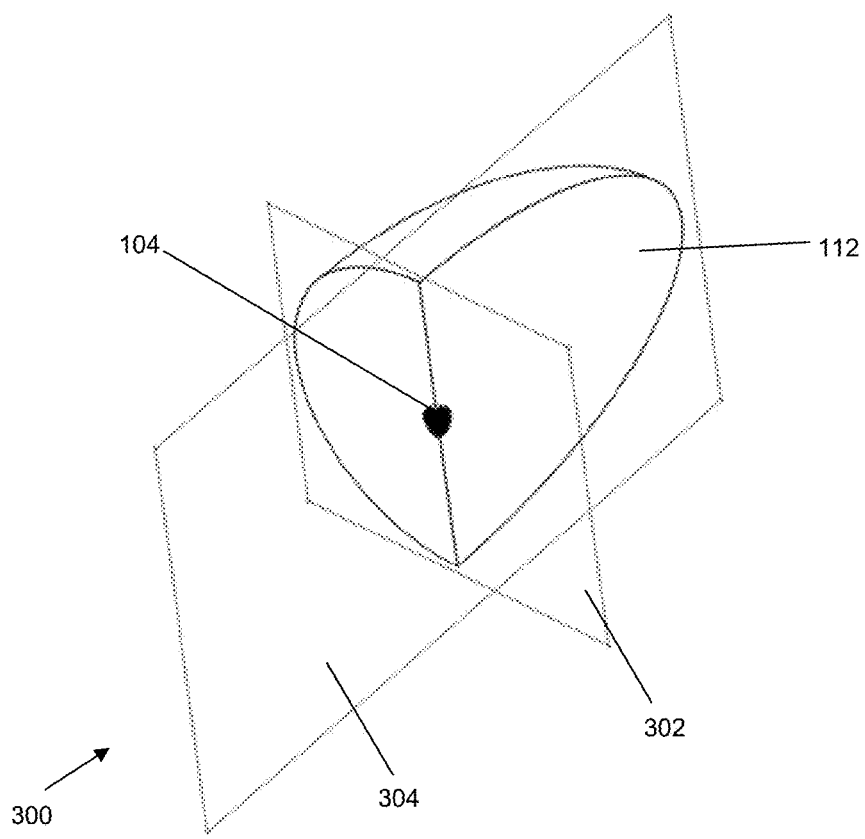
FIG. 3 shows a sectional view of a patient's body captured by a 3-dimensional (3D) imaging device according to an example embodiment.

FIG. 3 shows a sectional view 300 of a patient's body 112 (FIG. 1) captured by a 3D imaging device 110 (FIG. 1) according to an example embodiment. Here, a 3D image of the patient's body 112 is sectioned with two sectioning planes, i.e. x-axis plane 302 and y-axis plane 304, which pass through a kidney stone 104 (FIG. 1). The locations of the sectioning planes 302, 304 may be manually adjusted by a clinician for identifying the location of the kidney stone 104. As shown in this figure, the kidney stone 104 is clearly visible on the sectional view 300 as a result of the sectioning of the 3D image. This may allow the clinician to accurately select the kidney stone 104 and even the preferred location on the kidney stone 104 from the sectional view 300. A processor 114 (FIG. 1) subsequently determines the coordinates of the kidney stone 104 based on the location of the kidney stone 104 selected by the clinician and, according to the coordinates of the kidney stone 104, control an adjustment mechanism 106 (FIG. 1) to adjust the surgical tool 102 (FIG. 1) to align the longitudinal axis of the surgical tool 102 with the kidney stone 104.

Figure 4:
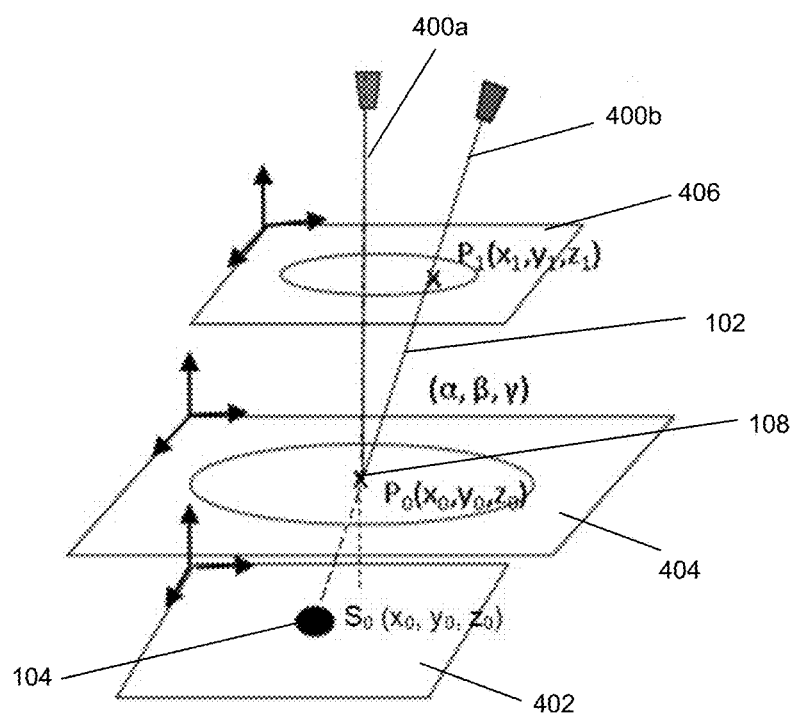
FIG. 4 shows a schematic diagram of a surgical tool being adjusted to align with a kidney stone according to an example embodiment.

FIG. 4 shows a schematic diagram of a surgical tool 102 (FIG. 1) being adjusted to align with a kidney stone 104 (FIG. 1) according to an example embodiment. As shown in FIG. 4, there are three planes involved in the adjustment of the surgical tool 102 from a first angular orientation 400a to a second angular orientation 400b, i.e. a target plane 402, a pivot point plane 404 and an adjustment mechanism plane 406.

As described above in respect of FIG. 1, the coordinates of the kidney stone 104 in the 3D Euclidean space, denoted by $S_0$ in FIG. 4, and the coordinates of the pivot point 108 (FIG. 1), denoted by $P_0$, can be extracted by the processor 114 from the 3D image received from the 3D imaging device 110 (FIG. 1). Using both coordinates $S_0$ and $P_0$, the processor 114 (FIG. 1) may calculate aligning coordinates on the plane 406, denoted by $P_1$, that align with the kidney stone 104 and the pivot point 108. For example, the coordinates $P_1$ correspond to the intersection between the straight line passing through the coordinates $S_0$ and $P_0$ and the plane 406. In other words, the aligning coordinates $P_1$ form a substantially straight line with the coordinates $S_0$ and $P_0$. Based on the aligning coordinates $P_1$, the processor 114 controls the adjustment mechanism 106 (FIG. 1) to adjust the surgical tool 102 at the adjustment mechanism plane 406 from the first angular orientation 400a to the second angular orientation 400b, such that the longitudinal axis of the surgical tool 102 passes through the aligning coordinates $P_1$ in the second angular orientation 400b. This can be done, for example, by moving the platform 206 laterally such that the ball joint compliance 210 is at the coordinates $P_1$. In the second angular orientation 400b, the longitudinal axis of the surgical tool 102 is aligned with the kidney stone 104 and the pivot point 108. The steps of determining the coordinates $S_0$ and $P_0$, calculating the aligning coordinates $P_1$ and adjusting the surgical tool 102 to align with the aligning coordinates $P_1$ may be repeated automatically to correct any errors until the longitudinal axis of the surgical tool 102 substantially aligns with the kidney stone 104.

Embodiments of the present invention provide a system and method for automatically aligning a surgical tool to a kidney stone. As described above with reference to the figures, the system determines the location data of the kidney stone and of the pivot point from the 3D image captured by the imaging device. According to these data, the system can make calculations to adjust the angular orientation of the surgical tool to align with the kidney stone. The system may also make calculations to determine the distance between the tip and the kidney stone and simulate a trajectory of the surgical tool, before inserting the surgical tool toward the kidney stone according to the distance calculated.

The 3D image captured by the 3D imaging device may be processed to generate sectional view of the patient's body. The accuracy of the kidney stone location determined by the system may be enhanced since the kidney stone is clearly visible on the sectional view. Further, the process of the surgical operation may also be simplified as compared to using conventional imaging device, as the 3D image provides the location data in 3D Euclidean space, allowing the system to calculate the accurate angular orientation and distance of the surgical tool with reference to the kidney stone before insertion of the surgical tool. This may eliminate the need for capturing multiple images from different angles in the conventional methods. As a result, embodiments of the present invention may enhance the accuracy of the trajectory of the surgical tool and reduce the surgical operation time, thus improving the rate of a successful operation.

Figure 5:
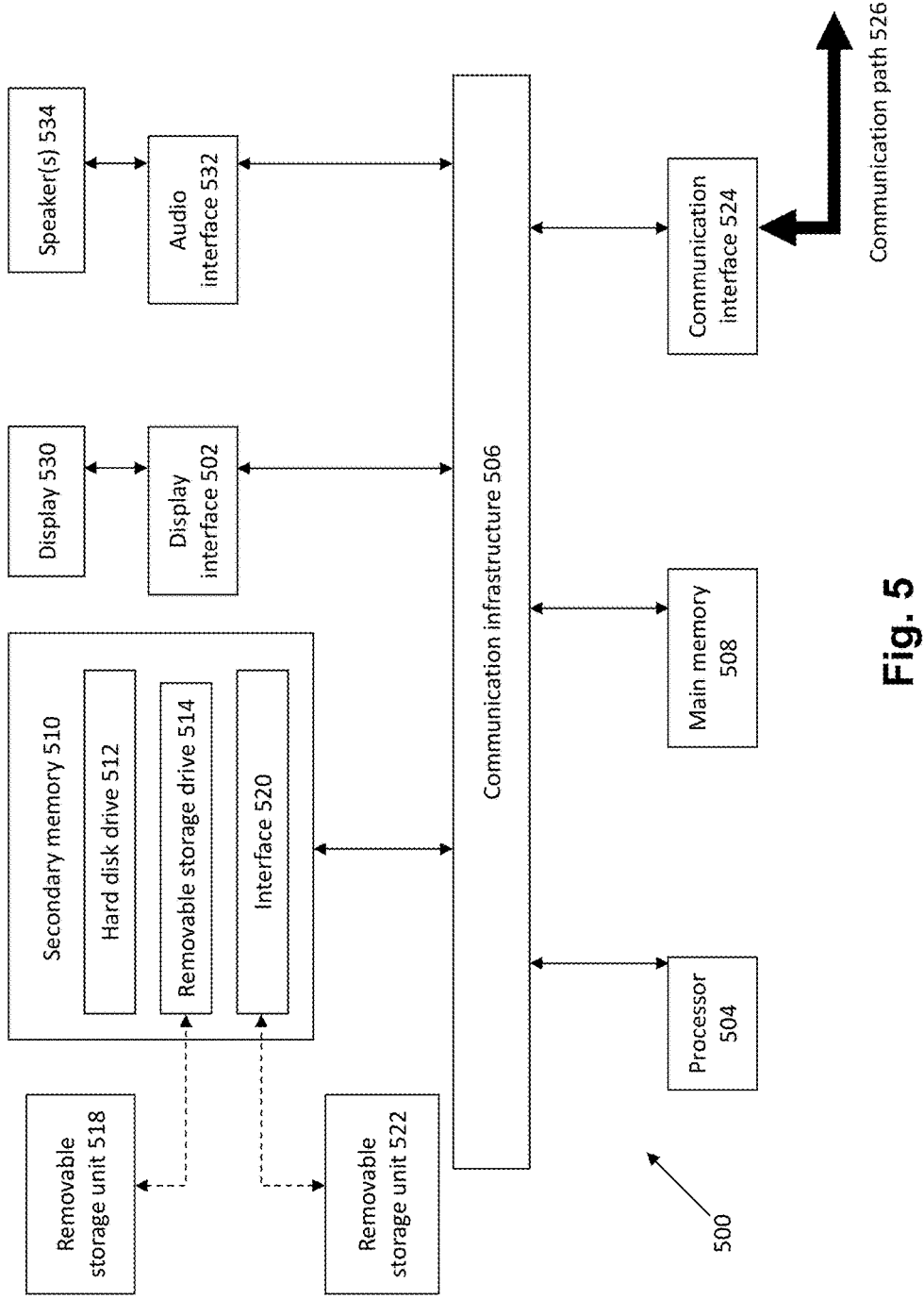
FIG. 5 shows an exemplary computing device suitable for use in the example embodiment.

FIG. 5 shows an exemplary computing device 500, hereinafter interchangeably referred to as a computer system 500, where one or more such computing devices 500 include processor (such as 114 in FIG. 1) for implementing the method and system of the example embodiments. The following description of the computing device 500 is provided by way of example only and is not intended to be limiting.

As shown in FIG. 5, the example computing device 500 includes a processor 504 for executing software routines. Although a single processor is shown for the sake of clarity, the computing device 500 may also include a multi-processor system. The processor 504 is connected to a communication infrastructure 506 for communication with other components of the computing device 500. The communication infrastructure 506 may include, for example, a communications bus, cross-bar, or network.

The computing device 500 further includes a main memory 508, such as a random access memory (RAM), and a secondary memory 510. The secondary memory 510 may include, for example, a hard disk drive 512 and/or a removable storage drive 514, which may include a floppy disk drive, a magnetic tape drive, an optical disk drive, or the like. The removable storage drive 514 reads from and/or writes to a removable storage unit 518 in a well-known manner. The removable storage unit 518 may include a floppy disk, magnetic tape, optical disk, or the like, which is read by and written to by removable storage drive 514. As will be appreciated by persons skilled in the relevant art(s), the removable storage unit 518 includes a computer readable storage medium having stored therein computer executable program code instructions and/or data.

In other embodiments, the secondary memory 510 may additionally or alternatively include other similar means for allowing computer programs or other instructions to be loaded into the computing device 500. Such means can include, for example, a removable storage unit 522 and an interface 520. Examples of a removable storage unit 522 and interface 520 include a program cartridge and cartridge interface (such as that found in video game console devices), a removable memory chip (such as an EPROM or PROM) and associated socket, and other removable storage units 522 and interfaces 520 which allow software and data to be transferred from the removable storage unit 522 to the computer system 500.

The computing device 500 also includes at least one communication interface 524. The communication interface 524 allows software and data to be transferred between computing device 500 and external devices via a communication path 526. In various embodiments of the inventions, the communication interface 524 permits data to be transferred between the computing device 500 and a data communication network, such as a public data or private data communication network. The communication interface 524 may be used to exchange data between different computing devices 500 which such computing devices 500 form part an interconnected computer network. Examples of a communication interface 524 can include a modem, a network interface (such as an Ethernet card), a communication port, an antenna with associated circuitry and the like. The communication interface 524 may be wired or may be wireless. Software and data transferred via the communication interface 524 are in the form of signals which can be electronic, electromagnetic, optical or other signals capable of being received by communication interface 524. These signals are provided to the communication interface via the communication path 526.

As shown in FIG. 5, the computing device 500 may further include a display interface 502 which performs operations for rendering images to an associated display 530 and an audio interface 532 for performing operations for playing audio content via associated speaker(s) 534.

As used herein, the term "computer program product" may refer, in part, to removable storage unit 518, removable storage unit 522, a hard disk installed in hard disk drive 512, or a carrier wave carrying software over communication path 526 (wireless link or cable) to communication interface 524. Computer readable storage media refers to any non-transitory tangible storage medium that provides recorded instructions and/or data to the computing device 500 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a SD card and the like, whether or not such devices are internal or external of the computing device 500. Examples of transitory or non-tangible computer readable transmission media that may also participate in the provision of software, application programs, instructions and/or data to the computing device 500 include radio or infra-red transmission channels as well as a network connection to another computer or networked device, and the Internet or Intranets including e-mail transmissions and information recorded on Websites and the like.

The computer programs (also called computer program code) are stored in main memory 508 and/or secondary memory 510. Computer programs can also be received via the communication interface 524. Such computer programs, when executed, enable the computing device 500 to perform one or more features of embodiments discussed herein. In various embodiments, the computer programs, when executed, enable the processor 504 to perform features of the above-described embodiments. Accordingly, such computer programs represent controllers of the computer system 500.

Software may be stored in a computer program product and loaded into the computing device 500 using the removable storage drive 514, the hard disk drive 512, or the interface 520. Alternatively, the computer program product may be downloaded to the computer system 500 over the communications path 526. The software, when executed by the processor 504, causes the computing device 500 to perform functions of embodiments described herein.

It is to be understood that the embodiment of FIG. 5 is presented merely by way of example. Therefore, in some embodiments one or more features of the computing device 500 may be omitted. Also, in some embodiments, one or more features of the computing device 500 may be combined together. Additionally, in some embodiments, one or more features of the computing device 500 may be split into one or more component parts.

It will be appreciated that the elements illustrated in FIG. 5 function to provide means for performing the various functions and operations of the servers as described in the above embodiments. In an implementation, a server may be generally described as a physical device comprising at least one processor and at least one memory including computer program code. The at least one memory and the computer program code are configured to, with the at least one processor, cause the physical device to perform the requisite operations.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A system for aligning an elongated tool to an occluded target, the system comprising:
   an adjustment mechanism configured to adjust an angular orientation of the elongated tool relative to a pivot point spaced from the target;
   a 3-dimensional (3D) imaging device configured to capture a 3D image of the elongated tool and the occluded target; and
   a processor communicatively coupled with the adjustment mechanism and the 3D imaging device, wherein the processor is configured to:
      process the 3D image received from the 3D imaging device to obtain location data of the target and the pivot point; and
      based on the location data of the target and the pivot point, control the adjustment mechanism to adjust the angular orientation of the elongated tool relative to the pivot point to align a longitudinal axis of the elongated tool with the target and the pivot point.

2. The system as claimed in claim 1, wherein the processor is further configured to:
   process the 3D image to generate a sectional view, wherein the sectional view comprises at least one sectioning plane passing through the target; and
   extract the location data of the target based on image data of the sectional view.

3. The system as claimed in claim 2, wherein the at least one sectioning plane comprises an x-axis sectioning plane and a y-axis sectioning plane perpendicular to the x-axis sectioning plane, and wherein both the x-axis and the y-axis sectioning planes pass through the target.

4. The system as claimed in claim 2, wherein the location data comprises target coordinates in 3D Euclidean space and wherein the processor is configured to extract the target coordinates based on the target location on the sectional view.

5. The system as claimed in claim 4, wherein the processor is further configured to:
   extract pivot point coordinates based on the 3D image;
   calculate a straight line passing through the target coordinates and the pivot point coordinates; and
   control the adjustment mechanism to adjust the angular orientation of the elongated tool to align the longitudinal axis of the surgical tool with the straight line.

6. The system as claimed in claim 5, wherein the processor is further configured to calculate a distance between the pivot point and the target based on the target coordinates and the pivot point coordinates.

7. The system as claimed in claim 6, wherein the processor is further configured to simulate a trajectory of the elongated tool toward the target using the distance and adjusted angular orientation of the elongated tool.

8. The system as claimed in claim 1, wherein the 3D image is a real-time 3D image and wherein the 3D imaging device comprises at least one selected from a group consisting of a magnetic resonance imaging (MRI) machine, a computerized tomography (CT) scanner and a fluoroscope.

9. The system as claimed in claim 1, wherein the adjustment mechanism comprises a base and a platform, wherein the platform is configured to be parallel to the base.

10. The system as claimed in claim 9, wherein the adjustment mechanism further comprises a plurality of arms linking the base with the platform, the plurality of arms being configured to move the platform along a plane parallel to the base to adjust the angular orientation of the elongated tool relative to the pivot point.

11. The system as claimed in claim 9, wherein the platform comprises a ball joint compliance for supporting the elongated tool, the ball joint compliance comprising a hole configured to allow sliding movement of the elongated tool therethrough.

12. The system as claimed in claim 9, wherein the adjustment mechanism further comprises a tool holder detachable from the platform.

13. A system for striking an occluded target using an elongated tool, the system comprising;
   an alignment system as claimed in claim 1; and
   an actuator coupled to the elongated tool, wherein the processor is further configured to determine a striking distance between the pivot point and the target; and
   wherein the actuator is configured to drive the elongated tool toward the target based on the angular orientation of the elongated tool at alignment and the striking distance.

14. The system as claimed in claim 13, further comprising a display device coupled to the processor, wherein the processor is further configured to simulate a trajectory of the elongated tool based on the angular orientation of the elongated tool at alignment and the striking distance for display on the display device.

15. The system as claimed in claim 13, further comprising a stopper configured to be mounted to the elongated tool and to prevent further movement of the elongated tool beyond the striking distance.

16. A method of aligning an elongated tool to an occluded target, the method comprising the steps of:
   capturing a 3-dimensional (3D) image of the elongated tool and the occluded target;
   processing the 3D image to obtain location data of the target and a pivot point spaced from the target; and
   based on the location data of the target and the pivot point, adjusting an angular orientation of the elongated tool relative to the pivot point to align a longitudinal axis of the elongated tool with the target and the pivot point.

17. The method as claimed in claim 16, wherein processing the 3D image to obtain location data of the target comprises the steps of:
   generating a sectional view, wherein the sectional view comprises at least one sectioning plane passing through the target; and
   extracting the location data of the target based on image data of the sectional view.

18. The method as claimed in claim 17, wherein the at least one sectioning plane comprises an x-axis sectioning plane and a y-axis sectioning plane perpendicular to the x-axis sectioning plane, and wherein both the x-axis and the y-axis sectioning planes pass through the target.

19. The method as claimed in claim 17, wherein extracting the location data of the target comprises extracting target coordinates in 3D Euclidean space based on the target location on the sectional view.

20. The method as claimed in claim 19, further comprising the steps of:
   extracting pivot point coordinates based on the 3D image;
   calculating a straight line passing through the target coordinates and the pivot point coordinates; and
   controlling the adjustment mechanism to adjust the angular orientation of the elongated tool to align the longitudinal axis of the surgical tool with the straight line.

* * * * *